United States Patent [19]

McVay

[11] Patent Number: 5,328,478
[45] Date of Patent: Jul. 12, 1994

[54] LAPAROSCOPIC IRRIGATION BOTTLE PUMP

[75] Inventor: William P. McVay, Doylestown, Pa.

[73] Assignee: Advanced Surgical Products, Inc., Miami, Fla.

[21] Appl. No.: 837,929

[22] Filed: Feb. 20, 1992

[51] Int. Cl.$^5$ ............................................. A61M 37/00
[52] U.S. Cl. ...................... 604/147; 604/65; 128/DIG. 12
[58] Field of Search .................. 604/30, 31, 35, 65-67, 604/140, 147; 128/DIG. 12, DIG. 13

[56] References Cited

U.S. PATENT DOCUMENTS

| 1,211,304 | 1/1917 | Farr | 604/147 |
|---|---|---|---|
| 2,693,801 | 11/1954 | Foreman | 128/DIG. 12 |
| 3,641,543 | 2/1972 | Rigby | 128/DIG. 13 |
| 3,648,694 | 3/1972 | Mogos et al. | 604/147 |
| 4,029,094 | 6/1977 | Winicki | 128/DIG. 12 |
| 4,117,843 | 10/1978 | Banko | 604/31 |
| 4,332,246 | 6/1982 | Thomson | 128/DIG. 12 |
| 4,460,353 | 7/1984 | Deckert et al. | 604/31 |
| 4,710,166 | 12/1987 | Thompson et al. | 604/65 |
| 4,718,576 | 1/1988 | Tamura et al. | 604/67 |
| 4,865,584 | 9/1989 | Epstein et al. | 604/67 |
| 4,872,872 | 10/1989 | Polak | 604/67 |
| 4,913,698 | 4/1990 | Ito et al. | 604/35 |
| 5,019,037 | 5/1991 | Wang et al. | 604/147 |

FOREIGN PATENT DOCUMENTS

| 563176 | 6/1977 | U.S.S.R. | 604/147 |
|---|---|---|---|
| 1496800 | 7/1989 | U.S.S.R. | 604/35 |

Primary Examiner—Ralph Lewis
Attorney, Agent, or Firm—Keck, Mahin & Cate

[57] ABSTRACT

A laparoscopic irrigation system and bottle pump for controlling a source of gas pressure driving a source of irrigation solution that includes a monitor for monitoring the gas pressure and indicating when the gas pressure falls below a predetermined value. Also, the liquid level of the source of irrigation solution is monitored and when the level falls to a predetermined value it is detected and a visual and an audible signal is actuated. Further the level of gas pressure driving the source of irrigation solution is controllable.

8 Claims, 3 Drawing Sheets

LAPAROSCOPIC IRRIGATION BOTTLE PUMP

FIELD OF INVENTION

The present invention relates to a laparoscopic irrigation bottle pump.

BACKGROUND OF INVENTION

Operative laparoscopy or pelviscopy is the use of a small rigid endoscope called a laparoscope in association with other instrumentation to view the organs of the abdomen via a 10 or 11 mm cannula or tube inserted through the abdominal wall, usually within the umbilicus. Additional puncture sites are created in the abdomen to pass instrumentation used to manipulate, cut, ligate, suture, staple, suction or irrigate a patient's abdominal contents.

A surgical instrument call a laparoscopic suction-irrigation probe (S/I Probe) is used for four functions: 1. blunt dissection, 2. irrigation of abdominal contents, 3. suctioning of smoke, water and debris from the abdominal cavity, and 4. the introduction of additional instrumentation for cutting or ligature. The S/I probe is a thin walled metal tube with a housing on the proximal end incorporating two trumpet valves and an entry port for additional instrumentation. The valves regulate the flow of irrigation solution and vacuum to the probe tip. The probe is connected to a sterile irrigation line which in turn is connected to an irrigation bottle of sterile normal saline or Ringer's solution. These solutions are either supplied in one liter or 1.5 liter semirigid thermoplastic bottles.

In order to push the solution from the bottle into the irrigation line, pressurized carbon dioxide ($CO_2$) gas is introduced into the closed bottle from a laparoscopic irrigation bottle pump. Currently, these irrigation bottle pumps are simply mechanical regulators connected to a toggle valve which allows the user to alternate the liquid flow to a second irrigation bottle when the first bottle becomes empty. The irrigation set incorporates two check valves to prevent the flow from the second bottle emptying into the first bottle and allows the user to exchange the empty bottle for a full one.

However, there are problems with these units. The user, who is usually an operating room nurse, must monitor the liquid level in the bottle so that the toggle valve can be switched at the proper time. If the nurse fails to closely monitor the bottle level, the bottle empties and the $CO_2$ gas will enter the irrigation line. If the line completely fills with gas, the operation is delayed while the irrigation line is purged of gas. This is annoying and time consuming to surgeons and nursing personnel and could be dangerous if too much gas inadvertently enters the abdomen.

A second problem can occur with these irrigation bottle pumps. The source of pressurized gas is usually an "E" size cylinder of $CO_2$, which is 24 to 29 inches tall, between 17 to 18 lbs. in weight and contains about 1240 liters of gas. Because of the nature of carbon dioxide the maximum cylinder pressure is 830 PSI (gage) at 70° F., which is the pressure at which carbon dioxide changes into a liquid state from a gas (known as vapor pressure). If a pressure gauge is used to monitor the amount of gas in the bottle, the pressure will stay at 830 PSI (gage) until all the liquid $CO_2$ in the bottle is exhausted. At this point the bottle contains about 208 liters of gas, which is less than 17% of the original filled volume. From this volume to when the cylinder is empty the pressure gauge drops as gas is used. Therefore, most of the time the cylinder pressure gauge does not budge since the vapor pressure maintains a gauge pressure of 830 PSI. If the gauge is not carefully monitored, the pump can run out of gas and delay the operation until a full cylinder is found and reconnected to the pump. Again, this is annoying and time consuming to nursing personnel.

Because of backlash within the screw mechanism of manually actuated pressure regulators, the selected pressure often drifts from the desired bottle pressure. The user must then readjust the regulator to compensate for this variance. Sometimes the drift can be as much as ±5 PSI.

SUMMARY OF INVENTION

To eliminate these problems a laparoscopic irrigation bottle pump has been conceived which is electronically monitored and controlled. The pump has the following features:

1. A potentiometer to accurately control the level of irrigation bottle pressure from 100 to 800 mm Hg (gage).
2. A LED digital display to indicate the irrigation bottle pressure.
3. Two liquid level sensors which monitor the amount of solution in each bottle and a control circuit which will automatically switch the gas head pressure to an alternative bottle when the active bottle is nearly empty.
4. Visual and audible alarms which caution the user to exchange the empty bottle for a full one.
5. Visual and audible alarms which caution the user when the $CO_2$ supply cylinder falls below 500 PSI (gage).

DETAILED DESCRIPTION OF PREFERRED EMBODIMENT

Figure 1:
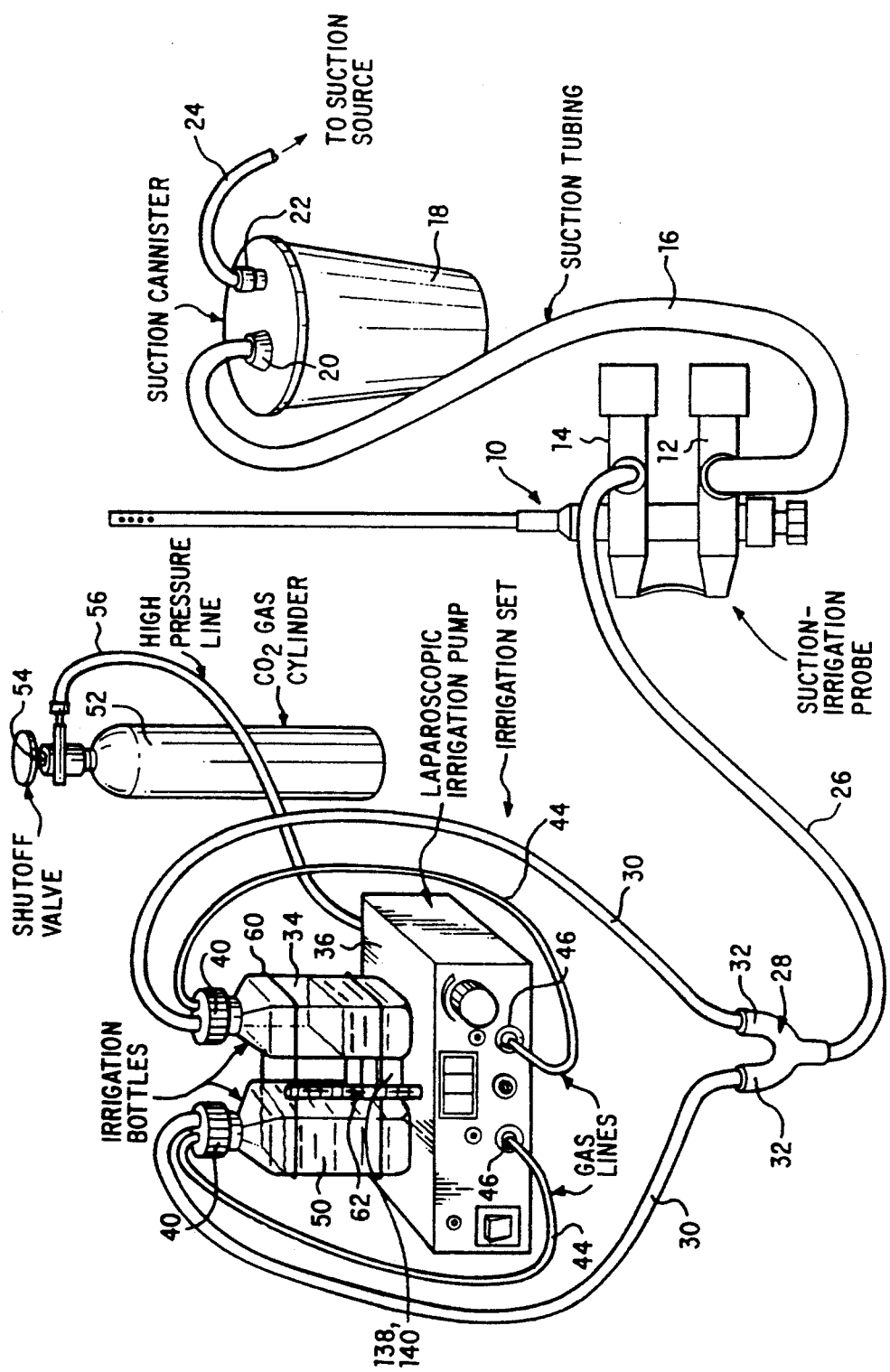
FIG. 1 is a perspective drawing of the novel laparoscopic irrigation pump system according to the present invention.

Referring to the drawings in detail FIG. 1 shows in perspective the novel system. As shown, a known suction-irrigation probe 10 having two trumpet valves 12, 14 is connected by suction tubing 16 leading from valve 12 to a suction cannister 18 via fitting 20. Cannister 18 is connected via fitting 22 and tubing 24 to a suction source (not shown). Tubing 26 leads from valve 14 to a wye branching connection 28. Tubing 30 leads from one branch 32 of connection 28 to an irrigation bottle 34 sitting on top of a housing 36 which contains the pump components. Tubing 30 connects to a fitting 38 which in turn is held in screw cap 40. Fitting 38, see FIG. 3, connects with a draw pipe or tube 42 that extends towards and terminates adjacent the bottom of bottle 34. A gas line 44 is detachably connected via a fitting 46 to housing 36 and leads to a fitting 48 in screw cap 40. A second bottle 50 is located on top of housing 36 spaced from bottle 34 and is connected the same way. A gas cylinder 52 containing $CO_2$ and provided with a shut-off valve 54 feeds high pressure gas via line 56 and an appropriate fitting to housing 36. Thus far all parts and connections are conventional and known.

Figure 3:
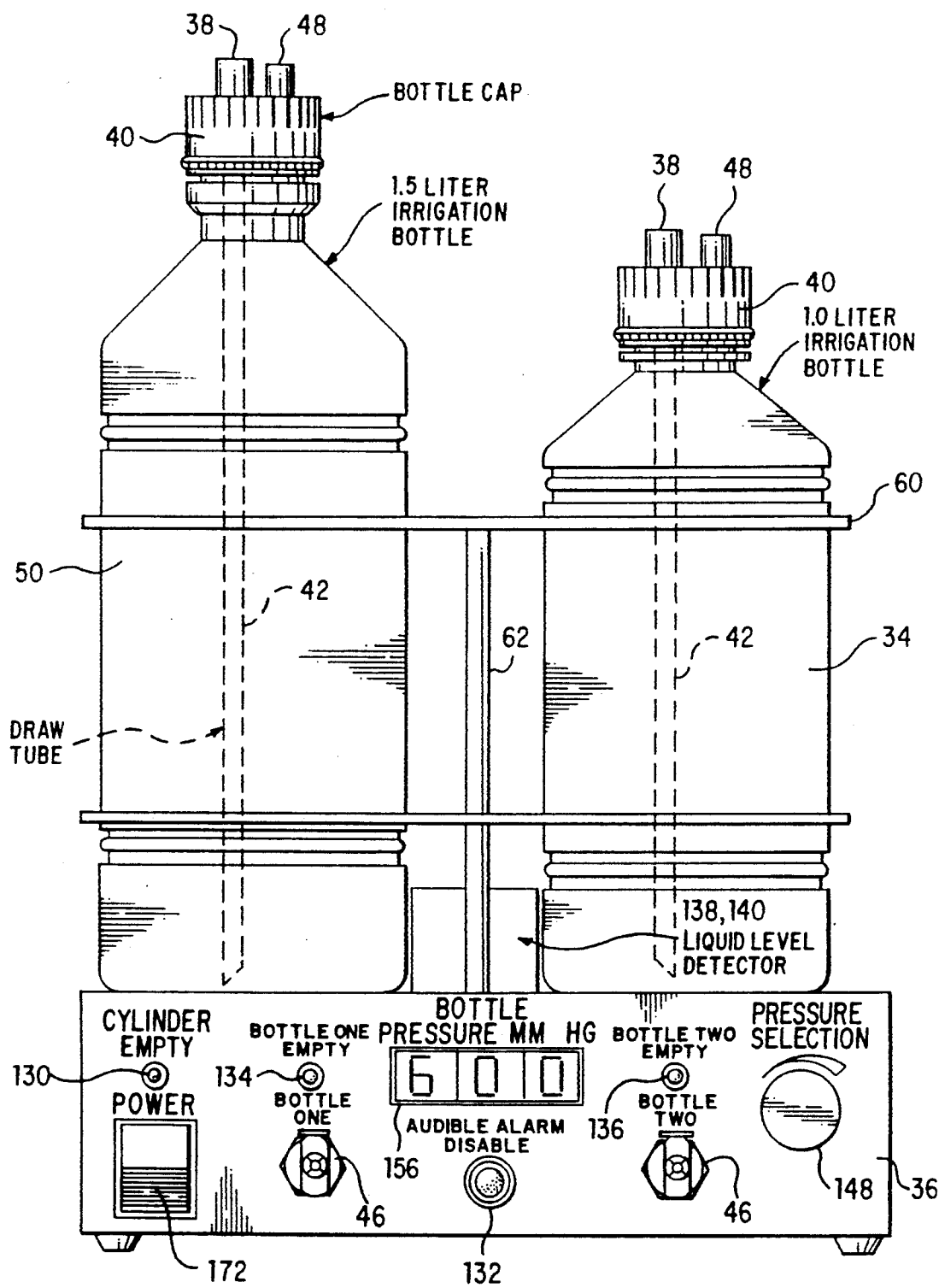
FIG. 3 is a front view of the laparoscopic irrigation pump.

A wire or rod frame 60 attached by posts 62 is mounted to the top of housing 36. A post 62 may have calibration markings on it to give an idea of liquid level in bottles 34, 50. Also, as illustrated in FIG. 3, bottles 34, 50 may be different size, e.g. 1 liter and 1.5 liter irrigation bottles.

Figure 2:
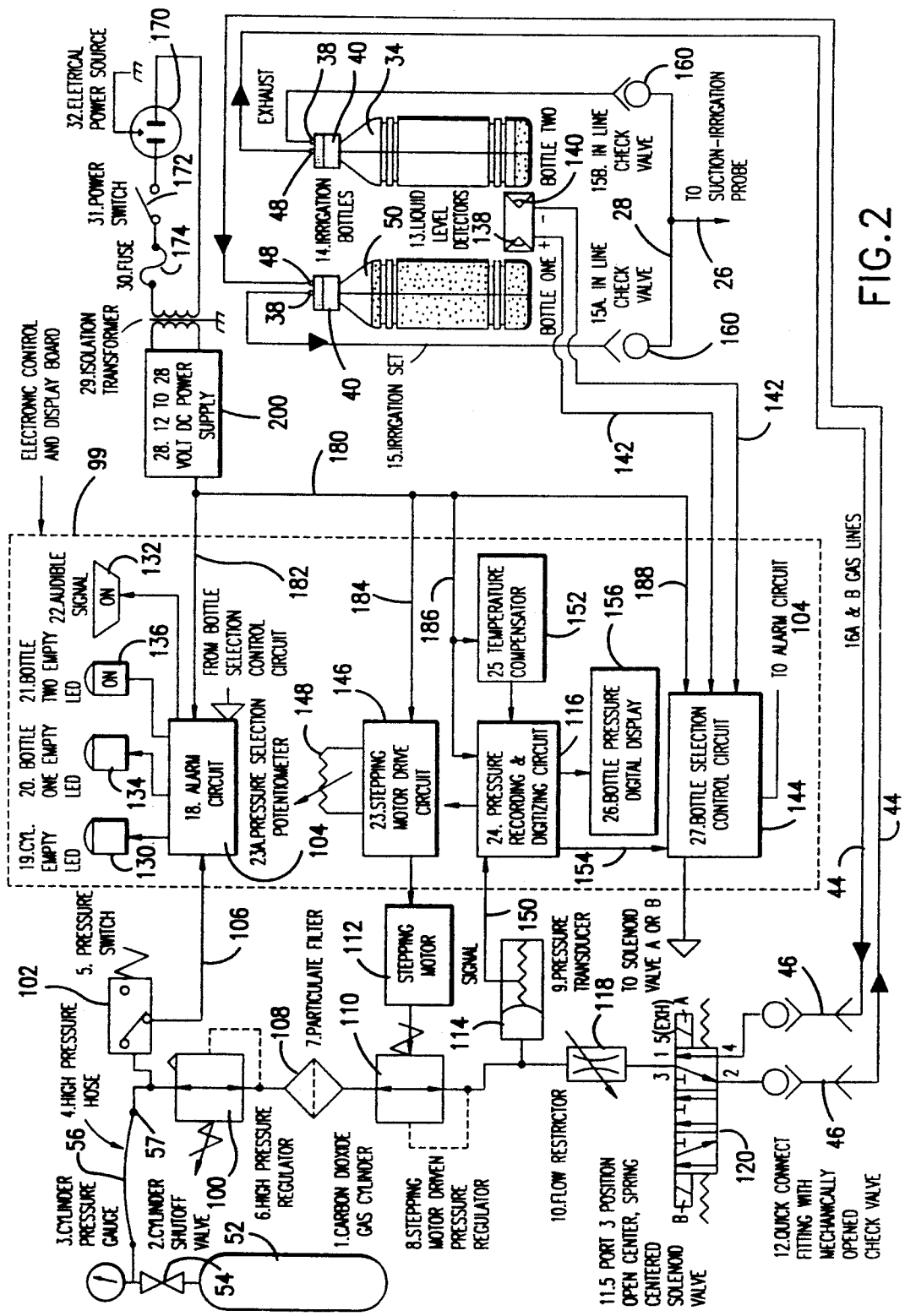
FIG. 2 is a schematic diagram of the pneumatic and electronic circuitry of the system.

Referring now to FIG. 2, the pneumatic components of the system will be described. High pressure $CO_2$ gas is introduced into housing 36 at point 57 via a suitable fitting and feeds to a pressure reducing regulator 100. The pressure in the line leading to regulator 100 is monitored by a pressure switch 102 with a reactive set point of 500 PSI. All pressures given herein are gage pressures. At this pressure a signal is sent to alarm circuit 104 via lead 106. An example of switch 102 is a unit that can be obtained from Whitman Controls Corp under model no. J705-3.

The pressure reducing regulator 100 has a maximum output pressure of 25 PSI. An example of regulator 100 is a unit that can be obtained under model no. PR-2 from GO, Inc. The output of regulator 100 is fed to an inline particulate filter 108 with a stainless steel mesh of 10 microns. An example of filter 108 is a unit that can be obtained from GO, Inc. identified as model F-4.

The output of filter 108 is fed to a pressure regulator 110 which is controlled by a stepping motor 112. The regulator 110 controls the downstream line pressure to between 6 and 16 PSI (300 to 800 mmHg) via step pulses induced into the bipolar stepping motor 112 causing the motor to turn a certain number of degrees of rotation either clockwise or counterclockwise. An example of regulator 110 is a stepping motor driven pressure regulator that can be obtained form Airtrol Components, Inc. under model no. SDU-5000/SDR-900-30.

Next the gas is monitored by an electronic pressure transducer 114 which proportionally converts gauge pressure to a certain voltage level and an electrical signal is output to a pressure recording and digitizing circuit 116. An example of a transducer to use is model SX30AN from SenSym, Inc.

The gas next flows through a gas flow restrictor 118 which limits the maximum gas flow to 6 liters/min. at 18 PSI driving pressure. An example of a restrictor is Model GRO-M5 from Festo Corp.

Next, the gas is controlled by a spool valve 120 actuated by two solenoids A and B which pull the spool valve to either end depending on which valve is opened. This deflects the gas flow to an alternative bottle while exhausting gas from the other irrigation bottle. If no power is provided to the valve 120, springs will center the spool which exhausts both bottles. Valve 120 is a 5 port 3 position open center, spring centered solenoid valve and an example of this unit is model no. W6057B2417 from the Ross Operating Valve Company.

The gas now flows through the two couplers 46 which are quick connect fittings with mechanically opened check valves and which connect the gas lines 44 alternatively to the bottle pump pneumatic circuit. An example of this coupler unit is one obtainable from Colder Products, Inc. under model no. PMCD16-02-12.

Now the electronic control and display board 99 will be explained. Alarm control circuit 104 which accepts a signal from pressure switch 102, via line 106, switches on, when appropriate, an LED indicator 130, marked "Cylinder Empty". Simultaneously, the circuit 104 turns on the audible alarm 132. This is a buzzer or bell which can be turned off and reset with a momentary pushbutton on the front panel (not numbered). The LED 130 will stay lit until the gas cylinder 52 is exchanged which resets the pressure switch 102. The alarm circuit 104 is also activated when either one of the liquid level detector signals is not present (−) from detectors 138, 140. This activates either "Bottle One Empty" LED 134 or "Bottle Two Empty" LED 136, as well as, the audible alarm 132. Liquid level detectors 138, 140 are positioned between the bottles 34, 50 to monitor and detect substantially empty condition of the bottles. The output from detectors 138, 140 is an electric signal that goes via lines 142 to a bottle selection control circuit 144.

A stepping motor drive circuit 146 sends step impulses to stepping motor 112 if manually operated pressure selection potentiometer 148 is changed. The circuit 146 compares the voltage signal from pressure recording circuit 116 to the voltage across potentiometer 148 and rotates stepping motor either CW or CCW depending on sign of voltage. When pressure transducer signal 150 balances the potentiometer voltage, the stepping motor 112 stops. The rate of change is proportional to the degree of difference of the comparative voltage levels.

The pressure recording and digitizing circuit 116 is a circuit which accepts the voltage signal 150 from transducer 114 and corrects the voltage signal for changes due to temperature using temperature compensator circuit 152. Circuit 116 amplifies the signal for output via line 154 to the bottle selection control circuit 144 and digitizes it for a conventional display circuit 156. The digital display 156 is a three segment LED numerical display which shown the bottle pressure in mmHg.

Bottle selection control circuit 144 is a logic control circuit which accepts input from liquid level detectors 138, 140 and sends signals to either solenoid coils, (valves) A or B, and to the alarm circuit 104. It also accepts input from pressure recording circuit 116 via line 154. The logic diagram for circuit 144 is as follows:

| Bottle Status | Detector Signals | | Solenoid Signal to |
|---|---|---|---|
| | One | Two | |
| Both Full | + | + | A |
| One Full, Two Empty | + | − | A |
| One Empty, Two Full | − | + | B |
| Both Empty | − | − | None |
| Pressure > PSI | any condition | | None |

Liquid level detectors 138, 140 use either known ultrasonic or photo detectors to noninvasively measure the presence of liquid at a certain height in the plastic irrigation bottle. If the liquid is below this preset level (approximately 1" level), the detector will not send a signal voltage to the bottle selection control circuit 114.

Bottles 34 and 50 contain standard sterile physiological solutions obtainable from either Baxter-Travenol Laboratories or Abbott Laboratories and the bottles are semirigid thermoplastic irrigation bottles.

The various tubing comprises an irrigation set made from $\frac{1}{4}"$ ID × $\frac{3}{8}"$ OD flexible PVC tubing. It incorporates molded plastic bottle caps with flexible PVC draw tubes, which are long enough for 1.5 liter bottles. Each leg from each bottle incorporates a check valve 160 to prevent the flow of solution from entering the empty bottle from the full one. The wye connection 28 feeds via tubing 26 to the probe 10.

Power to the pump is obtained from the mains via grounded plug 170 and feeds through power switch 172, fuse 174 and grounded isolation transformer 176 to a 12 to 28 volt DC power supply 200 of conventional design. The DC power is fed by lines 180, 182, 184, 186 and 188 to circuit 104, stepping motor drive circuit 146, pressure recording and digitizing circuit 116, temperature compensator 152 and bottle selection control circuit 144, respectively.

Although the invention has been described in terms of a preferred embodiment, changes are possible which do not depart from the spirit of the invention. Such changes fall within the purview of the invention as claimed.

What is claimed is:

1. A laparoscopic irrigation pump for controlling gas under pressure driving irrigation solution from a container comprising:
   first means for monitoring a source of gas under pressure and responsive to the gas pressure falling below a predetermined value to indicate same,
   second means for introducing gas under pressure into a container containing irrigation solution for driving the irrigation solution out of the container,
   third means for monitoring liquid level of irrigation solution in the container, detecting when the level falls to a predetermined value and responsive thereto terminating flow of the irrigation solution out of the container, and
   fourth means for receiving gas under pressure from the source, delivering gas to the second means and controlling the level of gas pressure delivery to the second means for introduction into the container for driving the irrigation solution out of the container, said fourth means including a pressure regulator for acting on gas from the source to adjust positive and negative deviations of the gas pressure to a predetermined level, a stepping motor connected to drive the regulator, a pressure transducer for sensing deviations of gas pressure on the output side of the pressure regulator correlated with said predetermined level of gas pressure and for converting same into corresponding electrical signals, control means acting responsive to said electric signals for controlling said stepping motor to restore the gas pressure on the output side of the pressure regulator to said predetermined level of gas pressure.

2. A pump according to claim 1 wherein the fourth means controls the pressure from about 100 to about 800 mm Hg (gage).

3. A pump according to claim 1 wherein the indications are visual.

4. A pump according to claim 1 wherein the indications are audible.

5. A pump according to claim 1 further including a digital display of the gas pressure.

6. A pump according to claim 1 wherein a plurality of containers containing irrigation solution are provided and said fourth means switches the gas pressure from one container of irrigation solution to another responsive to said third means.

7. A pump according to claim 1 wherein said fourth means includes temperature compensation means for compensating for changes in ambient temperature.

8. A pump according to claim 1, further including a manually settable control for setting the predetermined level of gas pressure and further control means for acting responsive to said manually settable control for controlling said stepping motor to adjust the pressure regulator.

* * * * *